United States Patent [19]
Rossi

[11] Patent Number: 5,460,204
[45] Date of Patent: Oct. 24, 1995

[54] STRIP OF COCKS

[75] Inventor: Daniel Rossi, Meriel, France

[73] Assignee: Vygon, Ecouen, France

[21] Appl. No.: 286,016

[22] Filed: Aug. 4, 1994

[30] Foreign Application Priority Data

Aug. 6, 1993 [FR] France .................................. 93 09721

[51] Int. Cl.[6] .................................................. F16K 11/00
[52] U.S. Cl. ........................................ 137/884; 137/271
[58] Field of Search ................................... 137/269, 271, 137/884

[56] References Cited

U.S. PATENT DOCUMENTS

| | | | |
|---|---|---|---|
| 3,477,469 | 11/1969 | Poley | 137/883 |
| 4,082,324 | 4/1978 | Obrecht | 137/271 X |
| 4,247,133 | 1/1981 | Moller | 137/271 X |
| 4,734,091 | 3/1988 | Boyle et al. | 137/883 X |

*Primary Examiner*—John C. Fox
*Attorney, Agent, or Firm*—Mason, Kolehmainen, Rathburn & Wyss

[57] ABSTRACT

The invention relates to strips of cocks. The strip is constituted by plates and by cocks, each plate being provided on two opposite edges with fastening portions enabling the plates to be fixed together end-to-end, and each plate carrying on at least one face one or more cocks or being provided on said face with means to which one or more cocks can be mounted, and each cock comprising a plug to which at least three endpieces secured to said plug open out, two of the endpieces, respectively a male endpiece and a female endpiece, being in alignment and opposite to each other on an axis that is perpendicular to said opposite edges of the plate once the cock is fixed on the plate, and the third endpiece being disposed obliquely or perpendicularly relative to the two aligned endpieces, said cock being designed to control fluid communication between the aligned endpieces and the third endpiece, and said aligned endpieces being designed so that said male and female endpieces engage mutually from cock to cock when the plates carrying the cocks are connected together end-to-end. The invention is particularly applicable to strips of cocks for medical use.

8 Claims, 3 Drawing Sheets

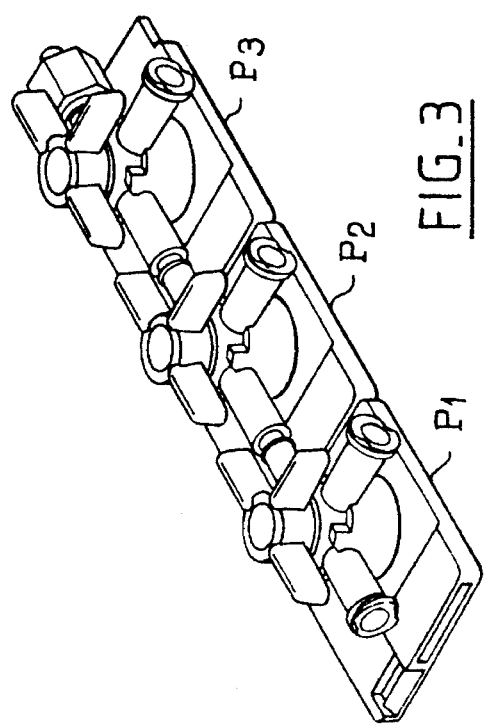
FIG_3
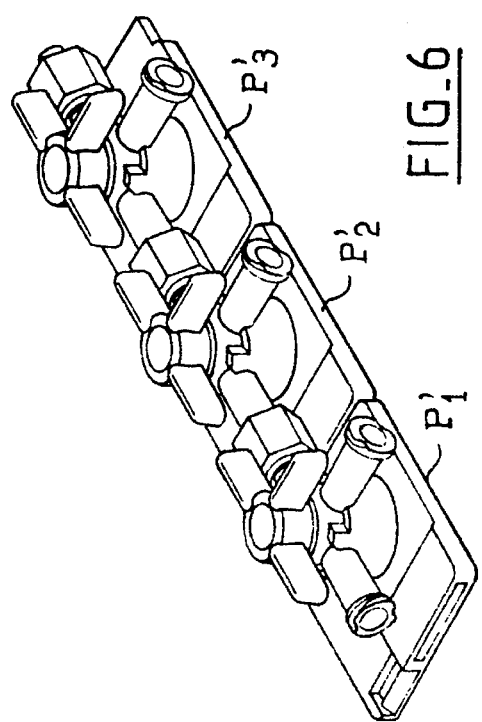
FIG_6
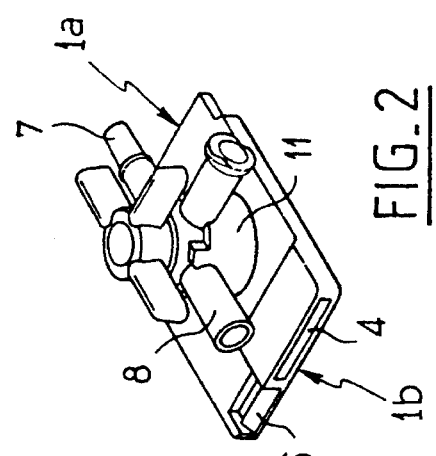
FIG_2
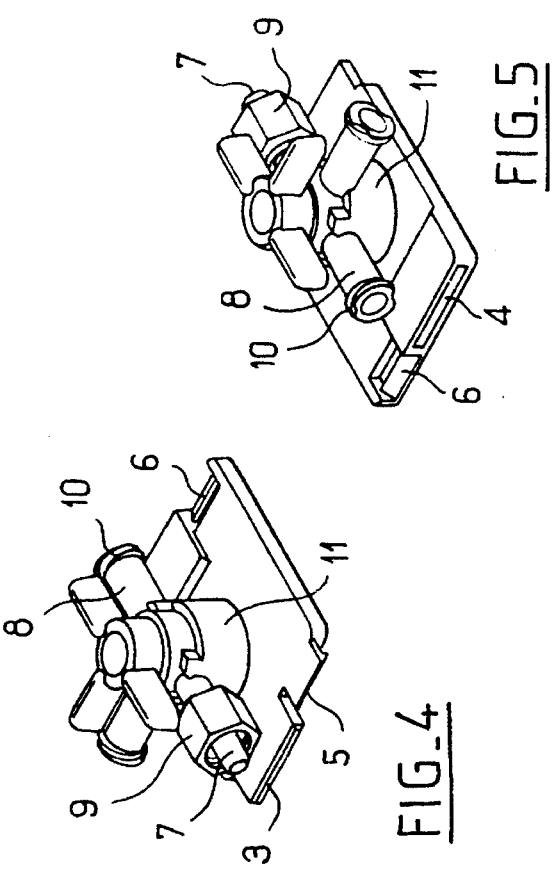
FIG_5
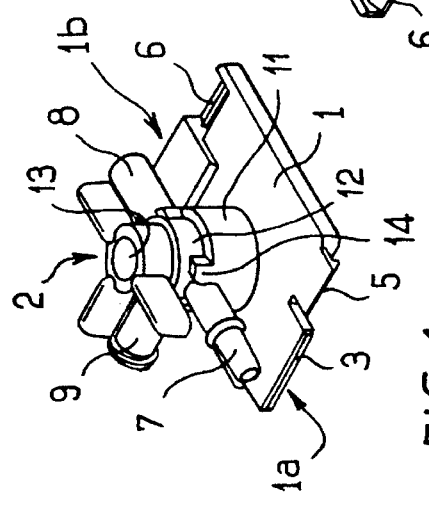
FIG_1
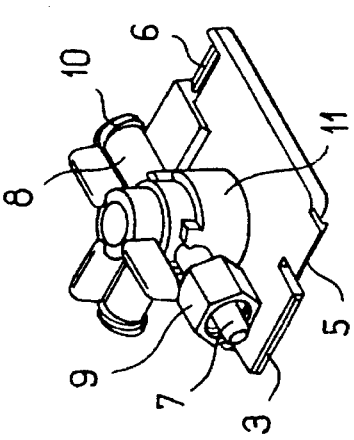
FIG_4

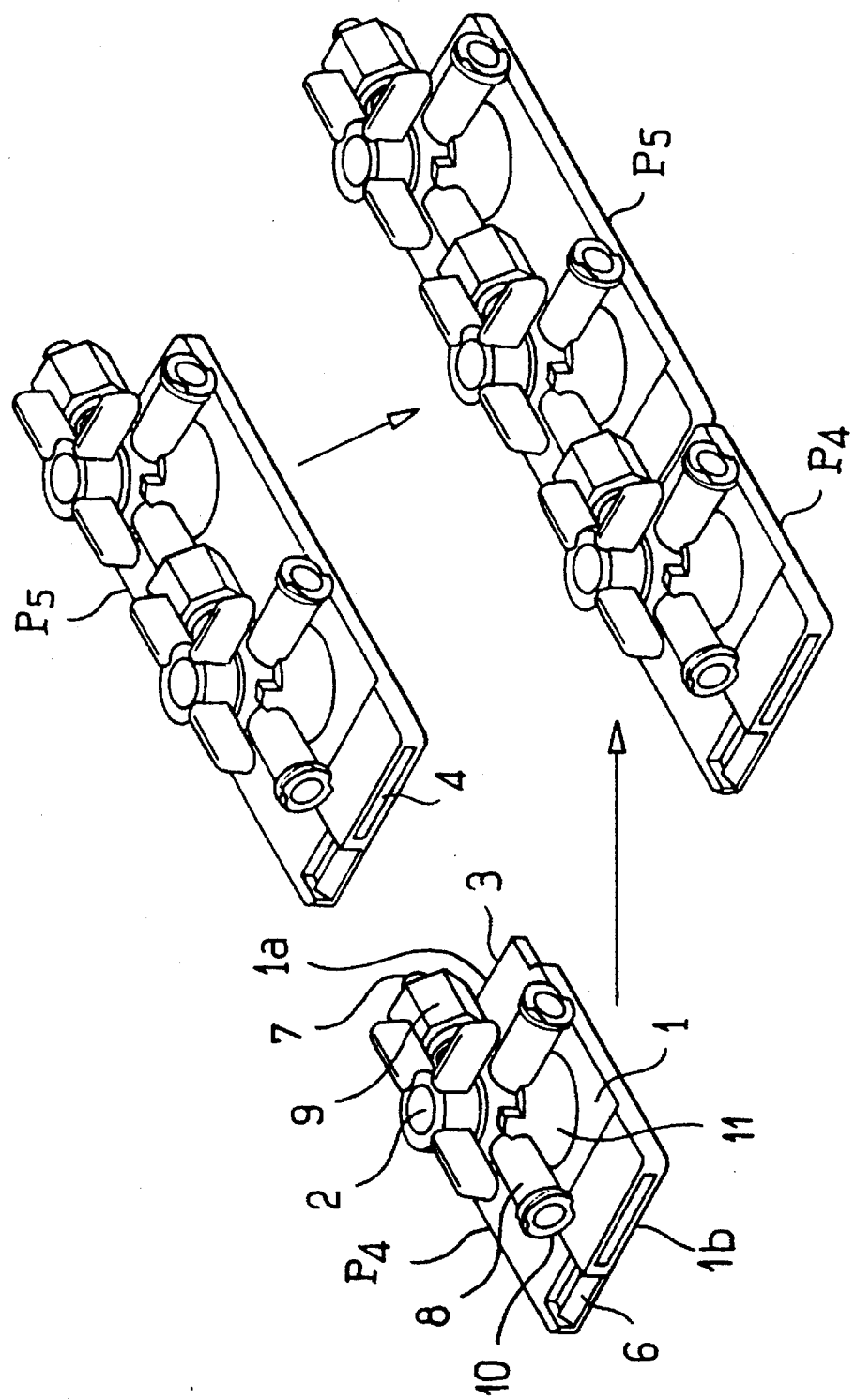
FIG_7

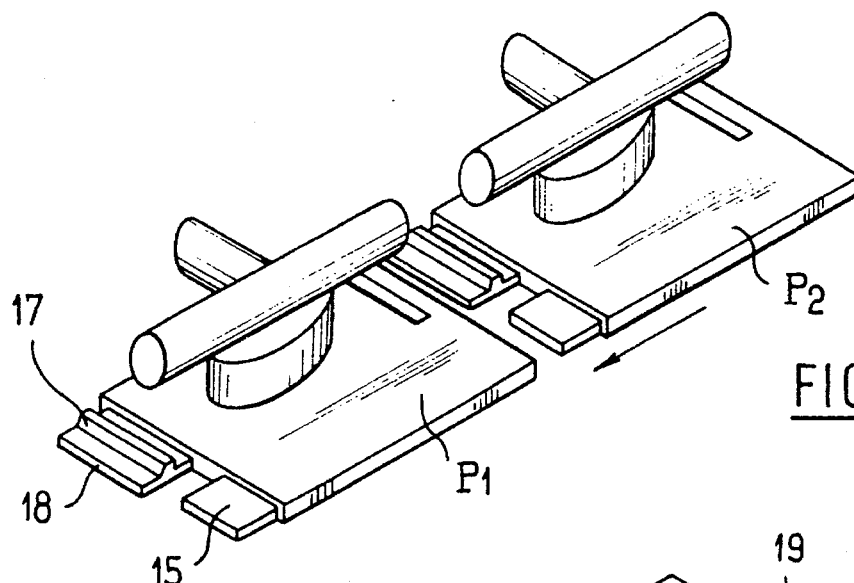
FIG_8
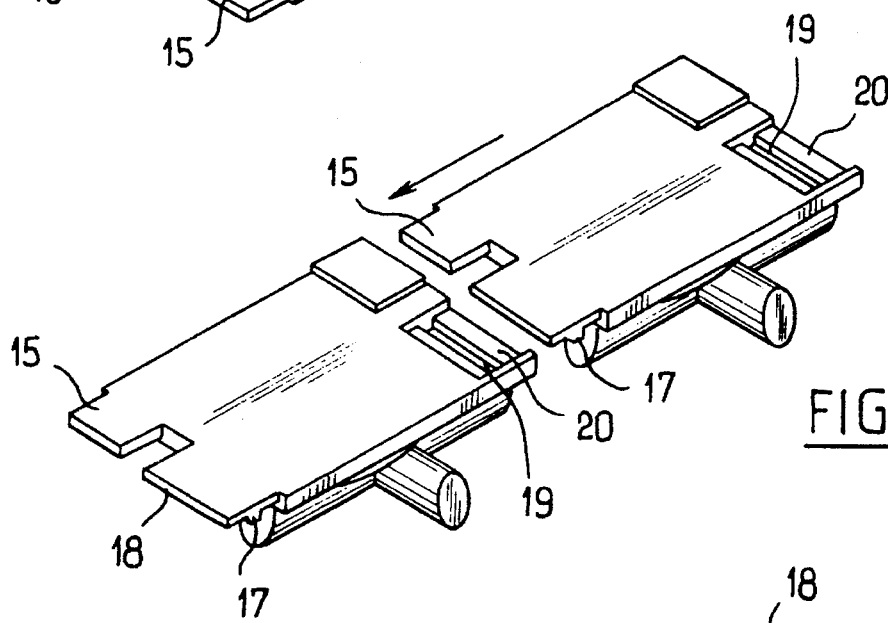
FIG_9
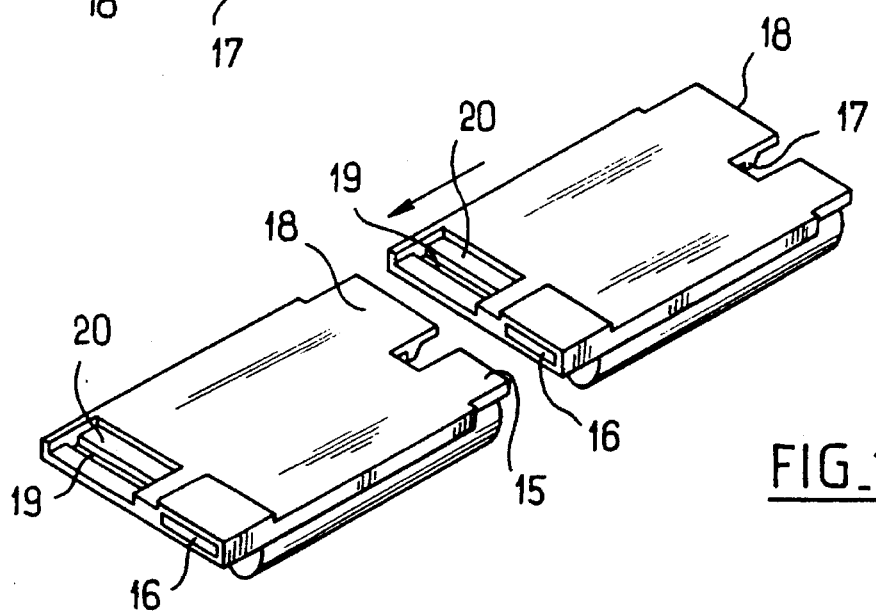
FIG_10

5,460,204

STRIP OF COCKS

FIELD OF THE INVENTION

The invention relates to strips of cocks as used particularly in the medical field for dispensing liquid on demand to one or more branches, where each branch is placed under the control of a cock.

OBJECT AND SUMMARY OF THE INVENTION

The object of the present invention is to facilitate the manufacture of such strips and also the use thereof, particularly by making it possible to vary the number of desired branches at will.

According to the invention, this is achieved by the strip being constituted by plates and by cocks, each plate being provided on two opposite edges with fastening means enabling the plates to be fixed together end-to-end, and each plate carrying on at least one face one or more cocks or being provided on said face with means to which one or more cocks can be mounted, and each cock comprising a plug to which at least three endpieces secured to said plug open out, two of the endpieces, respectively a male endpiece and a female endpiece, being in alignment and opposite to each other on an axis that is perpendicular to said opposite edges of the plate once the cock is fixed on the plate, and the third endpiece being disposed obliquely or perpendicularly relative to the two aligned endpieces, said cock being designed to control fluid communication between the aligned endpieces and the third endpiece, and said aligned endpieces being designed so that said male and female endpieces engage mutually from cock to cock when the plates carrying the cocks are connected together end-to-end.

It is thus possible to make a strip having an arbitrary number of paths, and to do so in the factory or in a hospital. It is even possible to start with a strip having x paths as manufactured in the factory and to add y single-cock plates thereto in a hospital so as to obtain a strip having (x+ y) paths.

From the industrial point of view, the invention makes it possible to restrict investment to a minimum while obtaining a high degree of commercial flexibility by adapting easily to variations in market demand.

The cocks may be fixed to one another by means of their male and female endpieces, e.g. using adhesive, welding, screw means, or snap-fastening. When screw means are used, the two aligned endpieces of a given cock respectively include a moving nut and an end with an outside thread, such that the nut-carrying endpiece of the cock on one plate can be secured to the threaded endpiece of the cock on an adjacent plate by screwing the nut onto the threaded end.

That configuration is the best adapted to assembly in a hospital, regardless of whether a strip is to be built up from scratch or whether additional paths are to be added to a strip that has been manufactured in a factory.

BRIEF DESCRIPTION OF THE DRAWINGS

Various structures of strips of the invention are described below with reference to the perspective views of the accompanying drawings, in which:

FIG. 1 shows a plate carrying a cock and together constituting a module for a strip;

FIG. 2 shows the module of FIG. 1 but facing in the opposite direction;

FIG. 3 shows a strip constituted by an assembly of modules of the type shown in FIG. 1;

FIG. 4 shows a variant module;

FIG. 5 shows the module of FIG. 4 facing in the opposite direction;

FIG. 6 shows a strip constituted by an assembly of modules of the type shown in FIG. 4;

FIG. 7 shows a variant strip;

FIG. 8 shows two modules constituting a variant embodiment of the invention, seen from above and in perspective;

FIG. 9 shows the two modules of FIG. 8, as seen from below and in perspective; and FIG. 10 is a view comparable to FIG. 9, but with the modules being shown the opposite way round.

MORE DETAILED DESCRIPTION

The module shown in FIG. 1 is constituted by a plate 1 of synthetic material, carrying a cock 2 likewise made of synthetic material.

On each of two opposite edges 1a and 1b, the plate is organized so as to be suitable for securing to the corresponding plate of a contiguous module placed upstream or downstream, with the plates being held together by mutual engagement and snap-fastening.

In this example, one of the edges 1a, has a tenon 3 while the opposite edge, 1b, presents a corresponding mortise 4. In addition, one of the edges, 1a, has a tongue terminated by a catch 5 while the other edge, 1b, has a tongue terminated by a catch 6, one of the two catches facing downwards and the other facing upwards. The catches of two contiguous plates co-operate by the fact of the two tongues carrying them presenting a certain degree of flexibility in a vertical plane.

It will be understood that the above fastening means are given purely by way of preferred example.

The cock is provided with two endpieces 7 and 8 that are in alignment on an axis parallel to the plate 1 and perpendicular to the snap-fastening edges 1a and 1b, and also with a third endpiece 9 that extends perpendicularly or obliquely relative to the aligned endpieces 7 and 8.

The endpiece 7 is a male Luer endpiece while the other endpiece 8 is a female Luer type endpiece, thereby enabling the endpieces of two contiguous plates 1 to be mutually engaged.

In the embodiment of FIGS. 4 and 5, the male endpiece 7 includes a moving nut 9 while the female endpiece 8 includes an end 10 having an outside thread such that the male endpiece 7 having the nut 9 on one module can be fixed to the threaded female endpiece 8 of the contiguous module by screwing the nut 9 onto the threaded end.

A plate 1 may carry one cock 2 or a plurality of cocks 2 disposed in line, which are fixed or fixable by any appropriate means, and indeed a plate 1 may carry cocks 2 on both faces.

For example, the plate 1 has a ring 11 on one of its faces into which the base 12 of the plug 13 of a cock 2 can be engaged. The cock 2 is held in place by jamming of its base or its endpieces. In the example shown, the ring 11 includes teeth 14 between which the endpieces 7 and 8 are jammed by force.

FIGS. 3, 6, and 7 show examples of strips made up by assembling together three identical plates ($P_1$, $P_2$, $P_3$; $P'_1$, $P'_2$, $P'_3$) (FIGS. 3 and 6), or two different plates ($P_4$, $P_5$), where one of the plates, $P_4$, carries a single cock while the other plate, P₅, carries two cocks. Clearly these examples are not limiting.

FIGS. 8 to 10 relate to a variant embodiment in which two plates (P₁, P₂) are assembled together by cooperation firstly between a tenon 15 projecting from an edge of one of the plates and a hollow housing 16 formed in the edge of the other plate, and secondly by a vertical rib 17 formed on a tongue 18 that projects from the edge of one of the plates and that co-operates with a vertical groove 19 in an end portion 20 of the other plate for the purpose of receiving said rib.

The invention is not limited to the above embodiments.

What is claimed is:

1. A strip of cocks comprising at least first and second plates and a plurality of cocks, each of said first and second plates being provided on first and second opposed edges with fastening means enabling said first and second plates to be fastened together end-to-end, said first plate having on at least one face thereof at least one of said cocks mounted thereon, and each of said cocks comprising a plug from which at least first, second and third endpieces project, said first endpiece being a male endpiece and said second endpiece being a female endpiece, said first and second endpieces being in alignment and opposite to each other on a first axis that is generally perpendicular to said first and second opposed edges of said first plate, and said third endpiece being disposed at an angle relative to said first and second endpieces so as to be disposed on a second axis that is not parallel to said first axis, said cock controlling fluid communication between said first and second endpieces and said third endpiece, and said first and second endpieces being adapted so that said first male endpiece on said cock engages a second female endpiece on said second plate when said first and second plates are connected together end-to-end.

2. A strip according to claim 1, wherein said fastening means comprises a tenon on said first edge of said first and second plates and a mortise on said second edge of said first and second plates.

3. A strip according to claim 1, wherein said fastening means comprise two catches, one of said catches being on said first edge of said first and second plates and the other of said catches being on said second edge of said first and second plates, said catches being positioned such that said catch on said first edge of said plate co-operates with said catch on a second edge of said second plate.

4. A strip according to claim 1, wherein said fastening means comprise a vertical rib on a tongue extending from said first edge of said first and second plates, and a vertical groove on said second edge of said first and second plates.

5. A strip according to claim 1, wherein the plates are integrally molded out of a synthetic resin.

6. A strip according to claim 1, wherein said first endpiece includes a moving nut and said second endpiece includes an outside thread, such that said nut on said first endpiece can be fixed to the outside thread on a second endpiece of anther cock on a contiguous plate by screwing the nut onto said outside thread on said second endpiece of said another cock.

7. A strip according to claim 1, including mounting means on said faces of said first and second plates for mounting said cocks thereon.

8. A strip according to claim 7, wherein said mounting means on each of said first and second plates includes at least one ring for receiving said plug of one of said plurality of said cocks.

* * * * *